US00PP32724P2

(12) United States Plant Patent
Durand

(10) Patent No.: US PP32,724 P2
(45) Date of Patent: Jan. 5, 2021

(54) ***SYRINGA* PLANT NAMED 'JEFTINI'**

(50) Latin Name: ***Syringa* x *prestoniae***
Varietal Denomination: Jeftini

(71) Applicant: James Richard Durand, West Kelowna (CA)

(72) Inventor: James Richard Durand, West Kelowna (CA)

(73) Assignee: JEFFRIES NURSERIES LTD, Portagela Prairie (CA)

( * ) Notice: Subject to any disclaimer, the term of this patent is extended or adjusted under 35 U.S.C. 154(b) by 0 days.

(21) Appl. No.: 16/873,812

(22) Filed: Jul. 14, 2020

(51) Int. Cl.
*A01H 5/00* (2018.01)

(52) U.S. Cl.
USPC ..... Plt./248

(58) Field of Classification Search
USPC ..... Plt./248
See application file for complete search history.

*Primary Examiner* — Annette H Para
(74) *Attorney, Agent, or Firm* — Penny J. Aguirre

(57) ABSTRACT

A new cultivar of *Syringa* plant named 'Jeftini' that is characterized by its compact and dense plant habit, reaching between 1.2 m and 1.5 m in height, its non-suckering growth habit, its large leaves with impressed veins on upper leaf surface and its fragrant, full panicles with bright pink flowers.

2 Drawing Sheets

Botanical classification: *Syringa* x *prestoniae*.
Variety denomination: 'Jeftini'.

BACKGROUND OF THE INVENTION

The present invention relates to a new and distinct cultivar of *Syringa* x *prestoniae* that is botanically known as *Syringa* 'Jeftini' and will be referred to hereafter by its cultivar name, 'Jeftini'. 'Jeftini' is a new cultivar of lilac grown for use as an ornamental landscape plant.

'Jeftini' arose from an on going breeding program conducted by the Inventor in Portage la Prairie, Manitoba, Canada. The objectives of the breeding program are to develop new cultivars of *Syringa* with a compact and dwarf plant habit, improved flowering and cold hardiness.

'Jeftini' originated as a cross made by the Inventor in June of 2007 between *Syringa* x *prestoniae* cultivars 'Charisma' (not patented) as the female parent and 'Miss Canada' (not patented) as the male parent. The Inventor selected 'Jeftini' as a single unique plant amongst the seedlings that resulted from the above cross in June of 2011.

Asexual propagation of the new cultivar was first accomplished by stem cuttings in June 2012 under the direction of the Inventor in Portage la Prairie, Manitoba, Canada. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Jeftini' as a unique cultivar of *Syringa*.

1. 'Jeftini' exhibits a compact and dense plant habit, reaching between 1.2 m and 1.5 m in height.
2. 'Jeftini' exhibits non-suckering growth habit.
3. 'Jeftini' exhibits large leaves with impressed veins on the upper surface.

4. 'Jeftini' exhibits fragrant, full panicles with bright pink flowers.

The female parent of 'Jeftini', differs from 'Jeftini' in having leaves that are smaller in size, flowers that are purple in color, panicles that are compressed and a more dwarf plant habit. The male parent of 'Jeftini', differs from 'Jeftini' in having a larger plant size and fewer flower panicles. The new *Syringa* can be most closely compared to *Syringa* x *prestoniae* cultivar 'Minuet' (not patented) and *Syringa patula* 'Miss Kim' (not patented). 'Minuet Preston' is similar to 'Jeftini' in having compact plant habit and large leaves with impressed veins. 'Minuet' differs from 'Jeftini' in having flowers that are lavender pink in color and a larger plant size at maturity. 'Miss Kim' is similar to 'Jeftini' in having a compact plant habit with a small stature and non-suckering growth habit. 'Miss Kim' differs from 'Jeftini' in having flowers that are lavender blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure includes but may not be limited to a website listing by Zosel Tree Farm.

BRIEF DESCRIPTION OF THE DRAWINGS

The accompanying colored photographs illustrate the overall appearance and distinct characteristics of the new *Syringa*.

The photograph in FIG. 1 was taken of a 5-year-old plant as grown in a trial garden in Cottage Grove, Minn. and provides a side view of a plant of 'Jeftini' in bloom.

Figure 1:
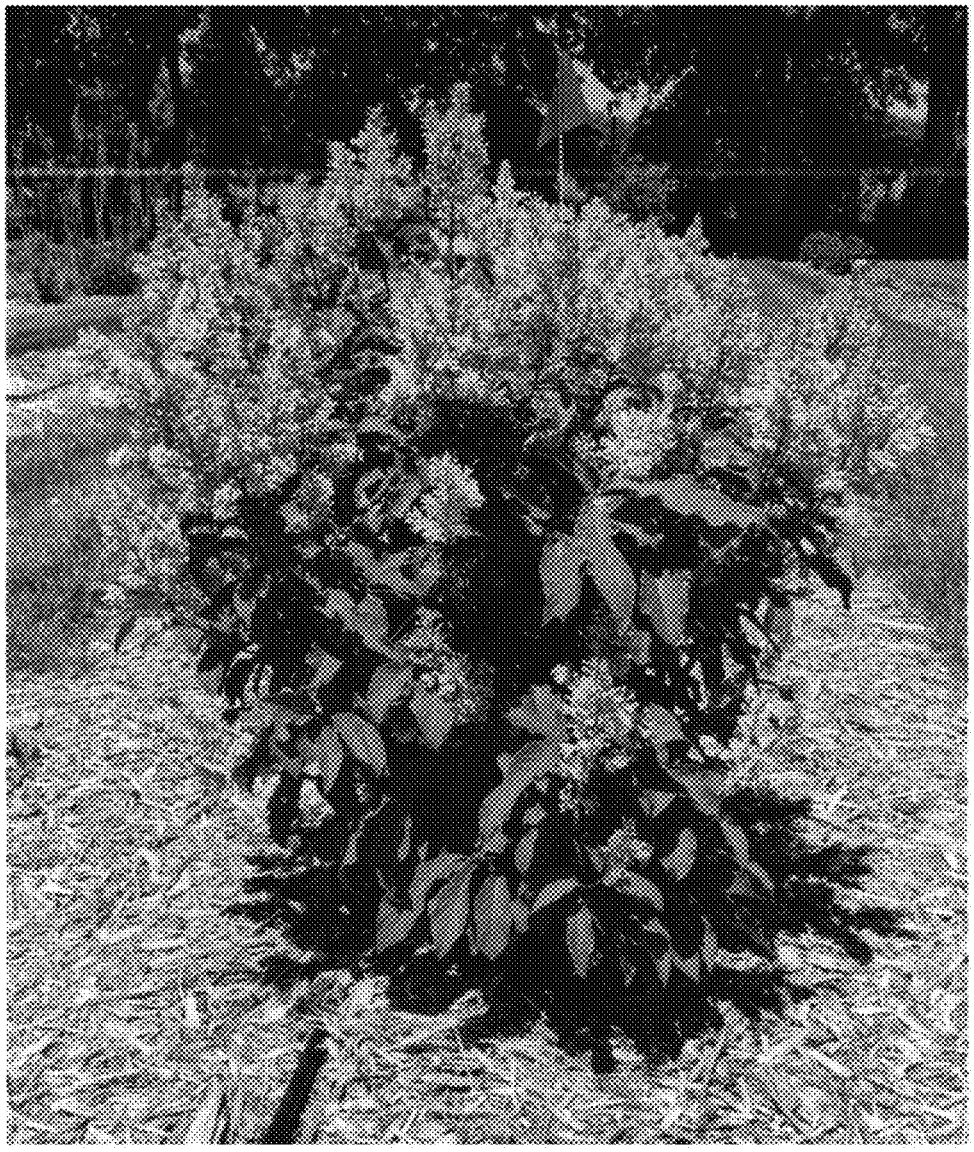
Figure 2:
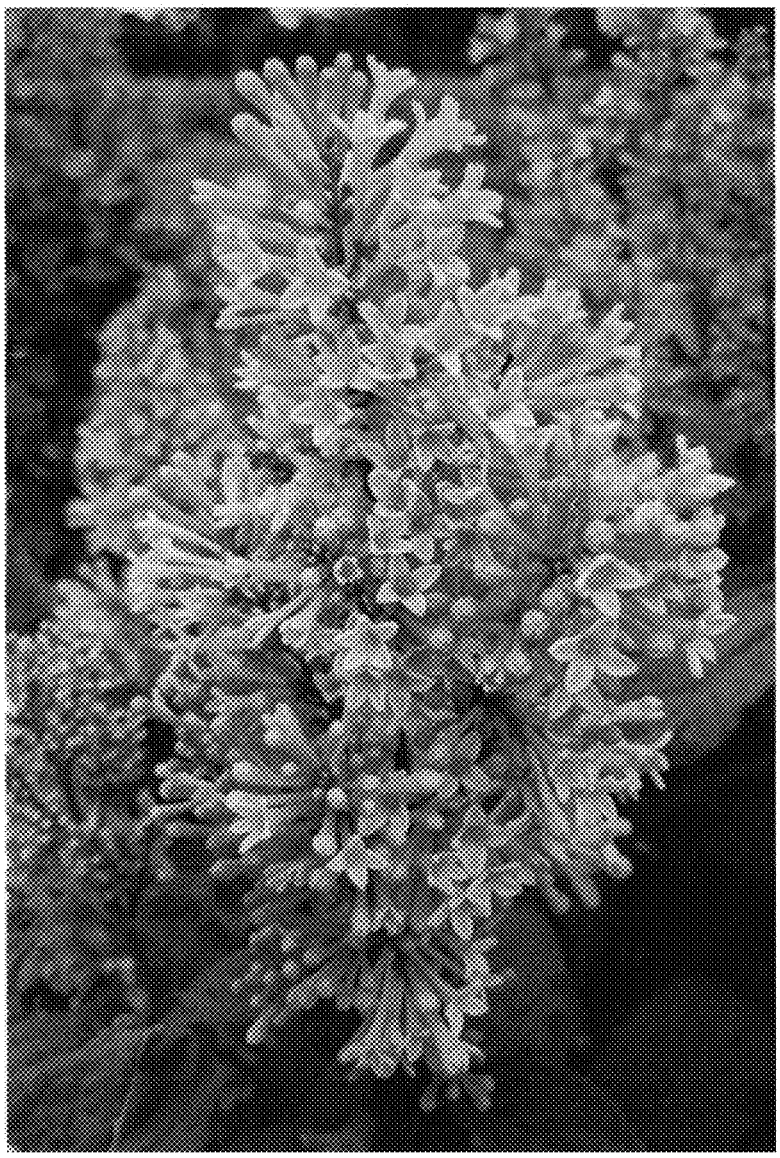

The photograph in FIG. 2 was taken of a plant 6-years in age as grown in a trial garden in Portage la Prairie, Manitoba, Canada and provides a close-up view of an inflorescence of 'Jeftini'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 5-year-old plants as grown outdoors in five-gallon containers in Cottage Grove, Minn. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—2 weeks in mid June in Canada.

*Plant type.*—Deciduous shrub.

*Plant habit.*—Compact, short statured.

*Height and spread.*—An average of 1.2 m to 1.5 m in height and 0.91 m to 1.2 m in width when mature in the landscape.

*Cold hardiness.*—At least in U.S.D.A. Zone 2.

*Diseases and pests.*—No resistance or susceptibility to diseases or pests has been observed.

*Root description.*—Fibrous and dense, a blend of 165A and 161D in color.

*Propagation.*—Softwood stem cuttings.

*Growth rate.*—Moderate.

*Root development.*—Roots intiate in 30 to 40 days, a young rooted plug liner is produced in about 75 days.

Branch description:

*Branch shape.*—Rounded.

*Branch color.*—Young; a blend of N144A, 148A, flushed with 178A, mature branches; a blend of 165A and 199A and 199D, mature wood; 199C and 201D.

*Branch size.*—Young lateral branches; average of 42 cm in length, 1 cm in diameter, main branches; 21 cm in length, 2 cm in width.

*Branch surface.*—Young branches; smooth and glabrous, moderately covered with lenticels, an average of 10 lenticels per cubic cm; 0.5 mm in diameter, 159C in color, mature branches; slightly rugose, slightly glossy and woody, moderately covered with lenticels; an average of 8 lenticels per cubic cm, 155A in color, an average of 0.5 mm in diameter, trunk; rugose, dull and bark-like.

*Branch quantity.*—Average of 2 main branches, average of 3 mature branches per main branches, average of 7 young lateral branches growing per mature branch.

*Internode length.*—6 cm in length.

*Branching.*—Held upright to slightly outward.

Foliage description:

*Leaf shape.*—Emerging elliptic, maturing into lanceolate.

*Leaf division.*—Simple.

*Leaf base.*—Acute.

*Leaf apex.*—Acuminate and acute.

*Leaf fragrance.*—None.

*Leaf venation.*—Pinnate, veins impressed on upper surface, upper surface color; matches leaf color and slightly transluscent, lower surface color; matches leaf color with main vein 178A in color.

*Leaf margins.*—Entire and slightly undulate, densely covered with minute pubescent stiff hairs that match the leaf color.

*Leaf arrangement.*—Opposite.

*Leaf attachment.*—Petiolate.

*Leaf surface.*—Upper surface matte, lower surface slightly glossy, both surfaces densely covered with very minute pubescent stiff hairs, transluscent to 155C in color.

*Leaf size.*—An average of 9 cm in length and 3 cm in width.

*Leaf quantity.*—An average of 48 leaves per mature branch.

*Leaf color.*—Young leaves upper and lower surface; transluscent, 144A, flushed with 176A.

*Petioles.*—An average of 1 cm in length and 1 mm in width, young petiote color 178A, mature petiole color 183A, both surface are glossy and moderately covered with minute pubescent stiff hairs transluscent to 155C in color.

*Bracts.*—An average of 2, at the base of a leaf cluster, an average of 5 mm in length and 2 mm in width, upper and lower surfaces; slightly glossy, slightly transluscent, 150D, margins 145A, tip flushed with 174A in color.

Inflorescence description:

*Inflorescence type.*—Thyrse compound panicles on terminals and laterals, broad ovate in overall shape.

*Inflorescence size.*—An average of 17 cm in length and 15 cm in width.

*Attitude of inflorescence.*—Upright to semi-upright.

*Rachis.*—Rounded in shape, up to 3 cm in length and an average of 2 mm in width, surface is glabrous, moderately strong, color is 144A with flushes of 179A, tiny lenticels densely cover the surface; average of <0.5 mm in length and NN155 in color, flushed around lenticels with 178A in color.

*Peduncles.*—An average of 3 cm in length and 2 mm in width, glabrous and slightly glossy surface, moderate strength, 144A in color and slightly flushed with 176A in color.

*Petioles.*—An average of 2 mm in length and 1 mm in width, surface glabrous, 144A in color and slightly flushed with 176A in color.

*Flower buds.*—Round to oval in shape, an average of 1 mm in length and 2 mm diameter, slightly glossy and glabrous surface, young bud color; 144C, flushed with 178A, mature bud color; 68A and 71A, base 69A

*Flower fragrance.*—Sweet, strong, lilac scent.

*Persistence of flowers.*—Self-cleaning, calyx persistent.

*Lastingness of flowers.*—Individual panicles bloom for about 2 weeks, depending on temperature.

*Flower quantity.*—An average of 500 flowers per compound panicle.

*Flower type.*—Salverform with spreading petals.

*Flower aspect*.—Upwards and outward.

*Flower size*.—An average of 1.5 cm in length, diameter 1 cm at apex, tapering to 1 mm at the base.

*Petals*.—4, free petal lobes; an average of 3 mm in length and 2 mm in width, oblong in shape with acute apices, entire margin, lower 80% fused forming a narrow tube, upper and lower surfaces smooth and glabrous, color; when opening inner and outer surface 75B flushed with 67A, when fully open inner and outer surface 67A, margins 75C and 75D, attitude semi-erect to drooping with apex slightly recurved.

*Flower tube*.—1 cm in length and 2 mm in width, inner and outer surfaces are smooth and globrous, color; when opening and fully open inner and outer surface 67A.

*Calyx*.—Campanulate, about 2 mm in depth and 1 mm in width, comprised of 4 fused sepals with tips unfused with acute apexes, glabrous inner and outer surface, 144C in color.

Reproductive organs:

*Pistils*.—1, inserted deep into calyx, average of 8 mm in length, stigma; 2 mm in length 1 mm in diameter, oval in shape, NN155D in color, style; NN155D in color.

*Stamens*.—3, extend beyond corolla, anthers; an average of 2 mm in length and 10A in color, filaments; about 1.3 cm in length and NN155D in color, translucent, pollen; abundant in quantity and 10A in color.

*Fruit and seed*.—No fruit or seed has been observed.

It is claimed:

1. A new and distinct cultivar of *Syringa* plant named 'Jeftini' as herein illustrated and described.

* * * * *